United States Patent [19]
Hamrick

[11] Patent Number: 5,492,285
[45] Date of Patent: Feb. 20, 1996

[54] MEDICAL STRETCHER HAVING RETRACTABLE STRAPS

[76] Inventor: Marcia L. Hamrick, 506 Forest Ridge Dr., Shelby, N.C. 28152

[21] Appl. No.: 358,677

[22] Filed: Dec. 19, 1994

Related U.S. Application Data

[63] Continuation of Ser. No. 64,631, May 20, 1993, abandoned.

[51] Int. Cl.⁶ .............................. B65M 75/48; A61F 5/37
[52] U.S. Cl. ...................... 242/379; 242/384.7; 128/876
[58] Field of Search ............................ 242/107, 107.4 R, 242/86.5 R, 86.7, 379, 384.7; 297/478, 479, 480; 5/424, 600, 621; 128/869, 875, 876; 200/61.58

[56] References Cited

U.S. PATENT DOCUMENTS

| | | | |
|---|---|---|---|
| 3,878,844 | 4/1975 | Tobias | 128/134 |
| 4,305,618 | 12/1981 | Molnar | 242/107.4 R X |
| 4,410,061 | 10/1983 | Terabayashi | 280/802 X |
| 4,427,164 | 1/1984 | Rumpf | 242/107.4 B X |
| 4,428,545 | 1/1984 | Naitoh | 242/107.4 R X |
| 4,569,095 | 2/1986 | Holling | 128/876 X |
| 4,699,132 | 10/1987 | Carville | 128/134 |
| 4,838,577 | 6/1989 | Kawai et al. | 242/107.4 A X |
| 4,970,739 | 11/1990 | Bradford | 5/628 X |
| 5,014,374 | 5/1991 | Williams | 5/81.1 |
| 5,040,740 | 8/1991 | DiPaola | 242/107.4 R |
| 5,192,035 | 3/1993 | Dufour | 242/107.4 R |

FOREIGN PATENT DOCUMENTS 1531504   12/1869   Germany .................. 242/107.4 R

*Primary Examiner*—John P. Darling

[57] ABSTRACT

A retractable strap apparatus for containing a strap which is commonly used on wheeled emergency tables and stretchers to secure a patient. The strap is wound around a spring loaded retracting mechanism which is contained within a cylindrical strap housing. The strap housing is mounted to a side of a wheeled emergency stretcher or table, and serves to contain the strap so as to prevent the strap from becoming entangled in a wheel of the stretcher or table. A group release for simultaneously releasing multiple straps and a loose strap alarm are also included in the design.

3 Claims, 4 Drawing Sheets

MEDICAL STRETCHER HAVING RETRACTABLE STRAPS

This application is a continuation of application Ser. No. 08/064,631, filed May 20, 1993, now abandoned.

BACKGROUND OF THE INVENTION

1. Field of the Invention

The present invention relates to straps and more particularly pertains to retractable straps which may be used on wheeled emergency tables and stretchers to secure a patient.

2. Description of the Prior Art

The use of stretcher straps is known in the prior art. More specifically, stretcher straps heretofore devised and utilized for the purpose of restraining and immobilizing a patient during transportation are known to consist basically of familiar, expected and obvious structural configurations, notwithstanding the myriad of designs encompassed by the crowded prior art which have been developed for the fulfillment of countless objectives and requirements.

For example, a restraint stretcher can be seen in U.S. Pat. No. 5,014,374 which includes a plurality of straps fastened to the stretcher to immobilize a patient during transport.

A similar stretcher is illustrated in U.S. Pat. No. 4,970,739 which utilizes straps to restrain a multiplicity of a patient's body parts, such as a patient's head and a patient's feet, during delivery to a medical facility so as to prevent further injury to the patient.

The stretcher straps mentioned above as a part of the foregoing patents serve the intended purpose of restraining or immobilizing a patient during transport, but in some situations all of the straps present on a given stretcher are not all used. For instance, when a small child is placed upon a stretcher, the straps near the foot area may be left unsecured. Or similarly, in a medical practitioner's haste to transport a patient, a strap may be left inadvertently unsecured. An unsecured strap may fall into a wheel of a transport cart that stretchers are commonly placed upon for movement, which may cause a potentially dangerous tangling of the strap within the wheel. Furthermore, many hospital and medical facilities utilize restraining straps on wheeled hospital beds, wheeled operating tables, and other wheeled patient transport structures that are presented with a similar potential danger of an unsecured strap engaging a rotating wheel.

Therefore, it can be appreciated that there exists a continuing need for a new retractable strap apparatus which can be utilized both to contain an unsecured strap and to alert a medical practitioner to the presence of such an unsecured strap. In this regard, the present invention substantially fulfills this need.

SUMMARY OF THE INVENTION

In view of the foregoing disadvantages inherent in the known types of stretcher straps now present in the prior art, the present invention provides a new retractable strap apparatus wherein the same can be utilized both to contain an unsecured strap and to alert a medical practitioner to the presence of an unsecured strap. As such, the general purpose of the present invention, which will be described subsequently in greater detail, is to provide a new retractable strap apparatus which has many of the advantages of the stretcher straps mentioned heretofore and many novel features that result in a retractable strap which is not anticipated, rendered obvious, suggested, or even implied by any of the prior art stretcher straps, either alone or in any combination thereof.

To attain this, the present invention essentially comprises a retractable strap apparatus for containing a holding strap which is commonly used on wheeled emergency tables and stretchers to secure a patient thereto. The strap is wound around a spring loaded retracting mechanism which is contained within a cylindrical strap housing. The strap housing is mounted to a side of a wheeled emergency stretcher or table and serves to contain the strap so as to prevent the strap from becoming entangled in a wheel of the stretcher or table. The strap can be locked into an extended position by a locking mechanism so that a snug fit around a patient may be achieved. A second embodiment of the present invention further includes a group release mechanism for simultaneously releasing a plurality of straps to expedite a release of a patient from such a stretcher or table. In addition, a third embodiment includes a loose strap alarm disposed within the strap housing for alerting a medical practitioner to a presence of an unsecured strap.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new retractable strap apparatus which has many of the advantages of the stretcher straps mentioned heretofore and many novel features that result in a retractable strap which is not anticipated, rendered obvious, suggested, or even implied by any of the prior art stretcher straps, either alone or in any combination thereof.

It is another object of the present invention to provide a new retractable strap apparatus which may be easily and efficiently manufactured and marketed.

It is a further object of the present invention to provide a new retractable strap apparatus which is of a durable and reliable construction.

An even further object of the present invention is to provide a new retractable strap apparatus which is susceptible of a low cost of manufacture with regard to both materials and labor, and which accordingly is then susceptible of low prices of sale to the consuming public, thereby making such retractable straps economically available to the buying public.

Still yet another object of the present invention is to provide a new retractable strap apparatus which provides in the apparatuses and methods of the prior art some of the advantages thereof, while simultaneously overcoming some of the disadvantages normally associated therewith.

Still another object of the present invention is to provide a new retractable strap apparatus which may be utilized to contain a strap that is commonly used on wheeled emergency tables and stretchers so as to prevent the strap from becoming entangled in a wheel of the stretcher or table.

Yet another object of the present invention is to provide a new retractable strap apparatus that may be easily mounted to a side of an existing wheeled emergency stretcher or table without substantial modifications thereof.

Even still another object of the present invention is to provide a new retractable strap apparatus that includes a group release mechanism for simultaneously releasing a plurality of straps.

Even still yet another object of the present invention is to provide a new retractable strap apparatus that includes a loose strap alarm for alerting a medical practitioner to a presence of an unsecured strap.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENTS

Figure 1:
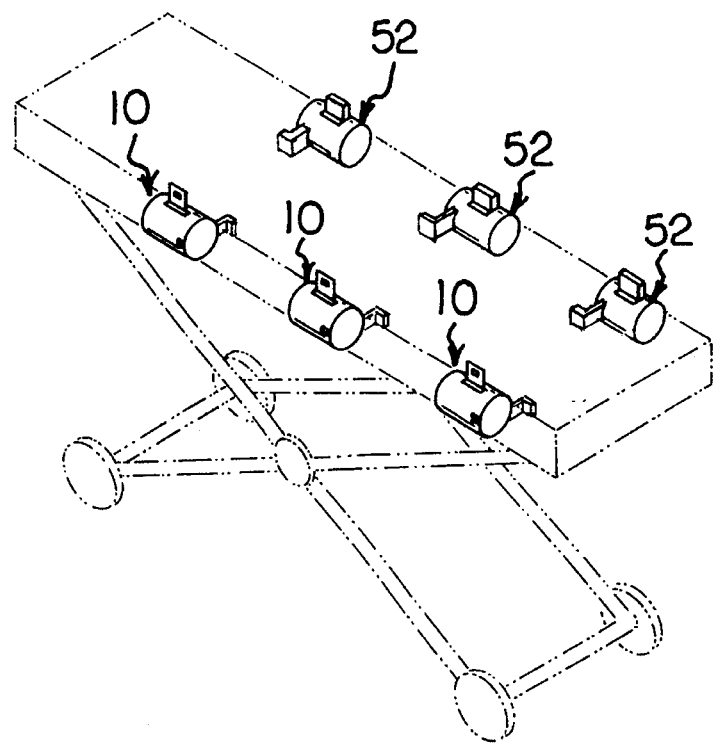
FIG. 1 is a perspective view of a plurality of retractable strap apparatuses comprising the present invention.
Figure 2:
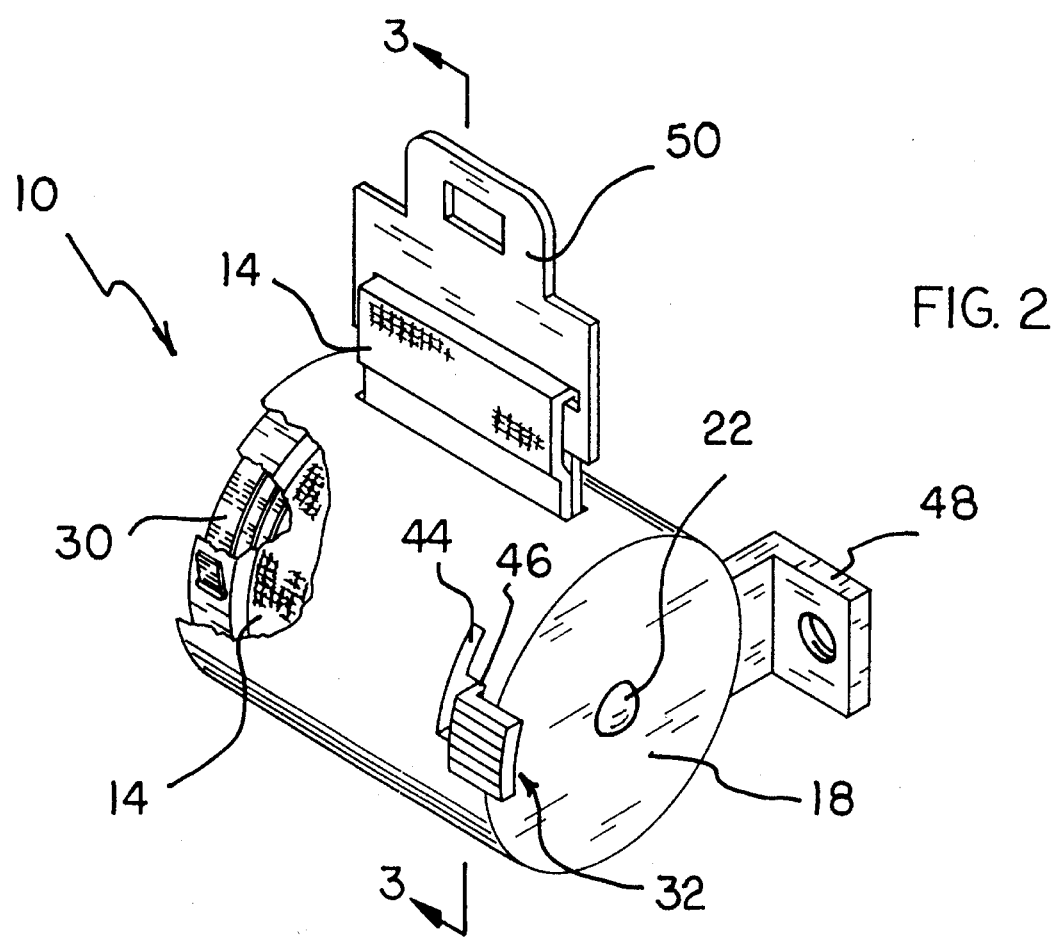
FIG. 2 is a perspective view of the present invention.
Figure 3:
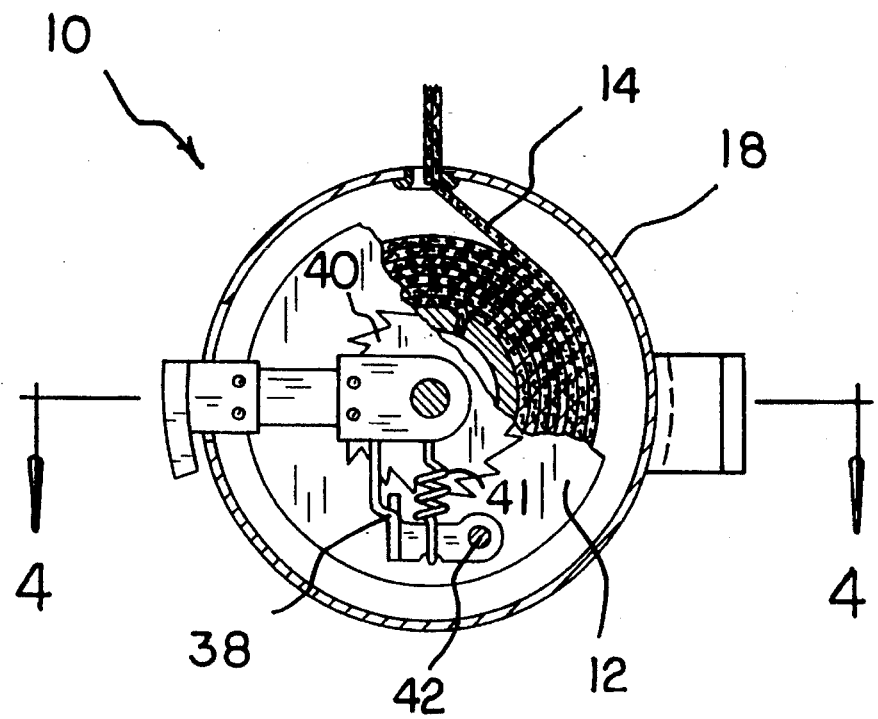
FIG. 3 is a cross sectional view taken along line 3—3 of FIG. 2.
Figure 4:
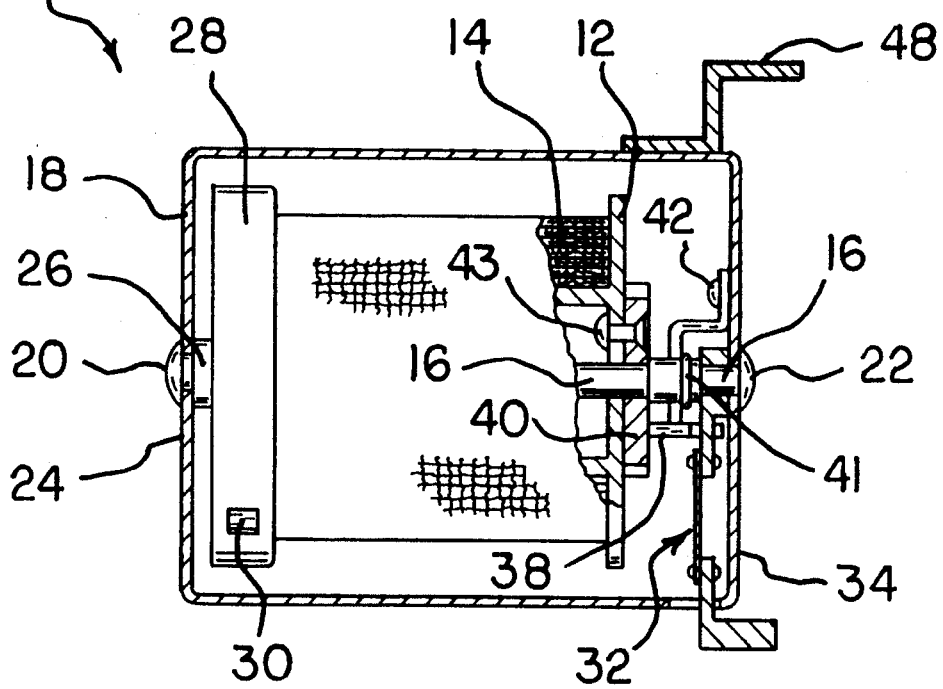
FIG. 4 is a cross sectional view taken along line 4—4 of FIG. 3.

With reference now to the drawings, and in particular to FIGS. 1–4 thereof, a first embodiment of a new retractable strap apparatus embodying the principles and concepts of the present invention and generally designated by the reference numeral 10 will be described.

More specifically, it will be noted that the retractable strap apparatus 10 comprises a spool 12 upon which a strap 14 is to be wound. The spool 12 is rotatably secured to an axle 16 so that the spool may revolve around the axle upon conventional bearing surfaces (not shown). The axle 16 is centrally and non-rotatably mounted within a spool container 18 by a pair of axle ends 20, 22. The spool 12 is distanced from a first end 24 of the spool container 18 by a spacer 26 that also serves as a bushing between the spool and the spool container so that the spool may freely rotate upon the axle 16. A spring retainer 28 for containing a spiral spring 30 is fixedly secured to the spool 12 proximate the first end 24 of the spool container 18. The spiral spring 30 is mounted in a conventional manner both to the spring retainer 28 and to the axle 16 so as to present a torque on the spool 12 that will cause the strap 14 to be wound onto the spool.

To facilitate control of the retracting apparatus, a release lever 32 is pivotably secured to the axle 16 proximate a second end 34 of the spool container 18. Coupled to the release lever 32 is a pawl 38 that may be selectively engaged to a ratchet 40. The pawl 38 is pivotably mounted to the spool container 18 by a pivot pin 42 and is biased towards the ratchet 40 by a spring 41. The ratchet 40 is fixedly secured to the spool 12 by at least one fastener 43. When engaged to the pawl 38, the ratchet 40 will allow for a single-direction rotation of the spool 12 upon the axle 16. Alternatively, the pawl 38 may be pivoted away from the ratchet 40 by the release lever 32 so as to allow for the unrestricted rotation of the spool 12 upon the axle 16. The release lever 32 extends outside of the spool container 18 through an aperture 44 that has a flange 46 integrally present therein. The flange 46 may be utilized to retain the release lever 32, thereby to selectively maintain the release of the pawl 38 from the ratchet 40.

The retractable strap apparatus 10 may be secured to any desired article, such as a medical stretcher and the like, by a mounting bracket 48 in a well understood manner. A catch 50 present at the end of the strap 14 may be engaged to a buckle 52 in a conventional manner. The buckle 52 is mounted to a side of the desired article and, because of its standard nature, will not be described in detail. The buckle 52 may be of any size and shape necessary to receive and securely retain the catch 50. However, the buckle 52 shown in FIG. 1 has a shape that substantially matches the overall appearance of the spool container 18 to provide for a pleasing and uniform appearance.

Figure 5:
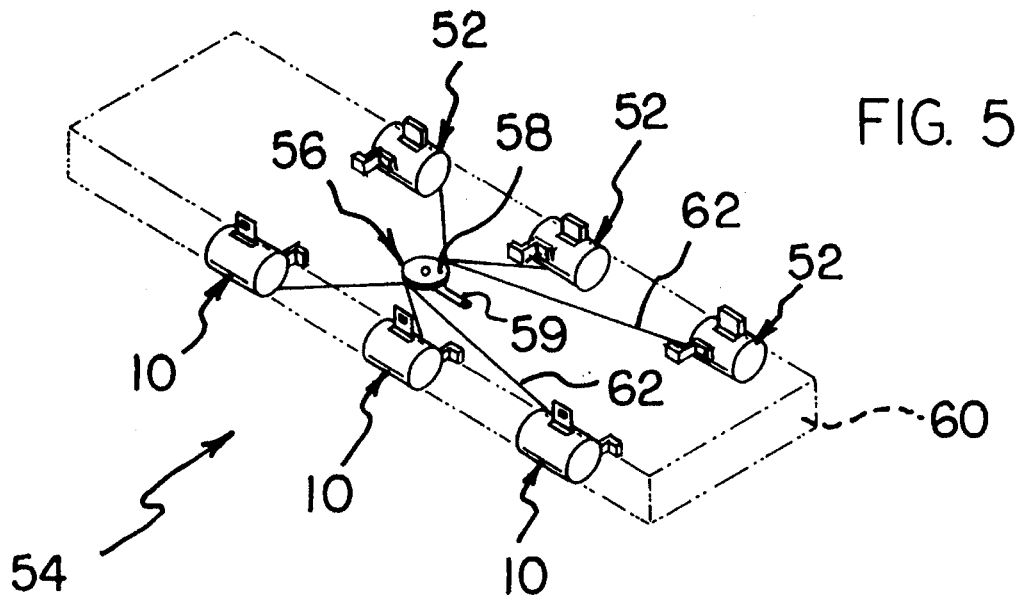
FIG. 5 is a perspective view of a second embodiment of the present invention.
Figure 6:
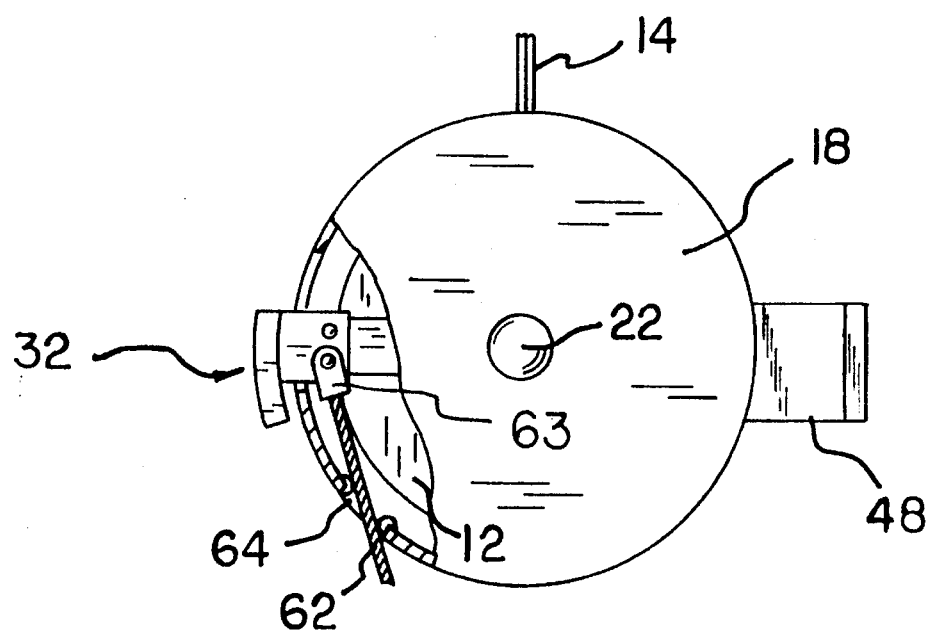
FIG. 6 is a side elevation view of the second embodiment with a portion of the side removed to show inside detail.

Referring now to FIGS. 5–6, a second embodiment of the present invention as generally designated by the reference numeral 54 comprises all of the features of the aforementioned embodiment 10 and further comprises an emergency release assembly 56 that is operable to release at least one retractable strap apparatus. The emergency release assembly 56 comprises a pulley 58 and a handle 59 for selectively rotating the pulley. The pulley 58 is rotatably mounted to a stretcher 60 or the like. The pulley 58 supports and secures a plurality of cables 62 that extend from the pulley in such a manner so as to create tension in the cables when the pulley is rotated in any direction. The cables 62 are operably connected both to at least one retractable strap apparatus 10 and to a respective buckle 52. When actuated, the emergency release assembly 56 causes a release of the catch 50 from the buckle 52 while simultaneously actuating the release lever 32 to allow the strap 14 to be retracted into the spool container 18. To facilitate the actuation of the release lever 32, an end 63 of one of the cables 62 passes through an aperture 64 in the spool container 18 and is connected to the release lever 32. In a substantially similar manner, additional cables may be connected to additional retractable strap apparatuses 10 and to their respective buckles 52.

Figure 7:
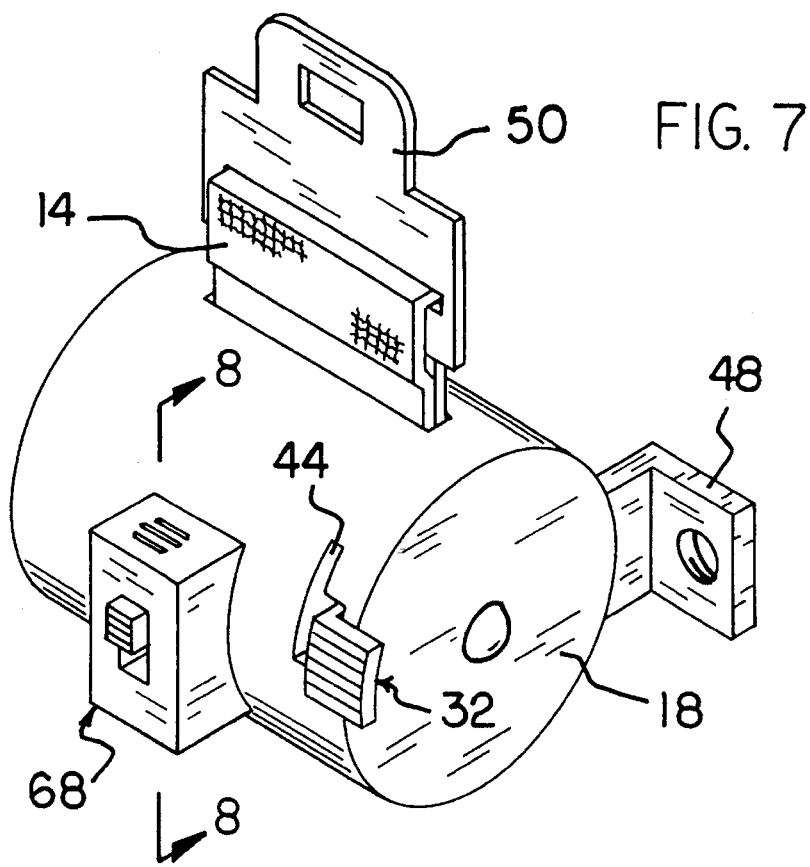
FIG. 7 is a perspective view of a third embodiment of a retractable strap apparatus comprising the present invention.
Figure 8:
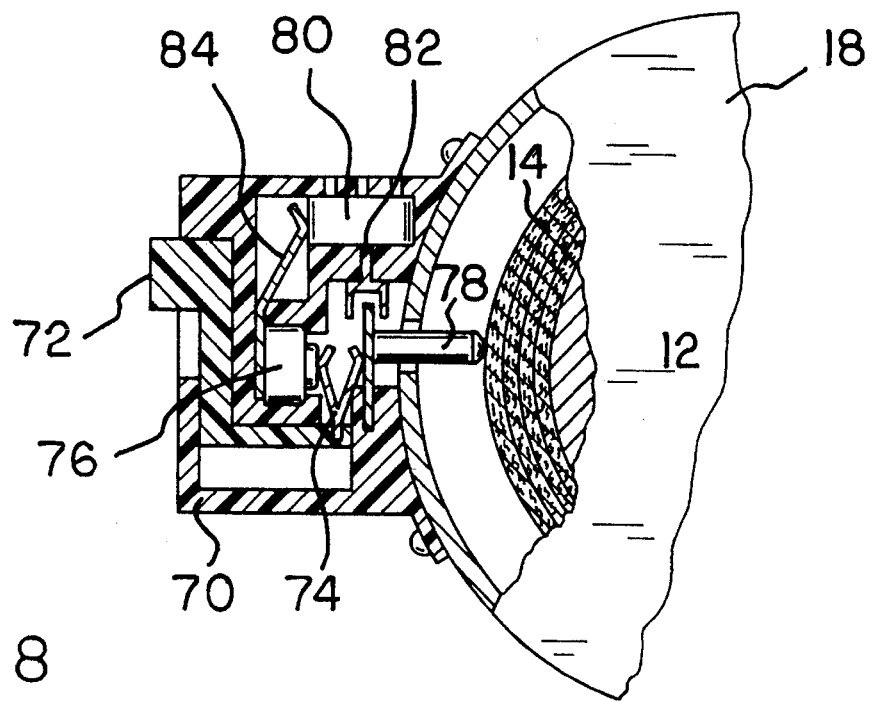
FIG. 8 is a partial cross sectional view taken along line 8—8 of FIG. 7.

With reference now to FIGS. 7–8, a third embodiment 66 of the present invention will now be described. The third embodiment 66 comprises all of the features of the two foregoing embodiments 10, 54 and further comprises an alarm assembly 68 for alerting a medical practitioner to the presence of an unsecured strap 14. The alarm assembly 68 is attached to the spool container 18 and comprises an alarm body 70 and a switch 72 that is slidably disposed within the alarm body. The switch 72 extends outside of the alarm body 70 and is selectively operable by a user to advance a bridge 74 into contact with a battery 76 and a plunger 78. The plunger 78 extends into the spool container 18 and is positioned proximate the spool 12. The bridge 74 and the plunger 78 are both at least partially comprised of an electrically conductive material, whereby electric potential may be selectively transferred from a high potential side of the battery 76 through both the bridge and the plunger to a beeper 80. An electrical contact 84 is connected to both a low potential side of the battery 76 and the beeper 80. When the strap 14 is substantially wound upon the spool 12, the plunger will contact the strap and be biased towards an electrical contact 82 on the beeper 80, thereby completing the circuit and actuating the beeper.

As to the manner of usage and operation of the present invention, the same should be apparent from the above description. Accordingly, no further discussion relating to the manner of usage and operation will be provided.

In summary, the retractable strap apparatus replaces the plain straps which are commonly present on wheeled stretchers and tables with straps that are wound around a spring loaded retracting mechanism inside of a cylindrical housing. Therefore, when the straps are not fastened around a patient, they are automatically wound back inside of the housing. The movement of the patient is never hindered by a strap that has become entangled in a wheel. In addition, the emergency release assembly and the alarm assembly serve both to allow a quick removal of a plurality of straps and to alert a medical practitioner of an unsecured strap, respectively.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A retractable strap apparatus comprising:

a medical stretcher;

a plurality of retractable strap assemblies secured to said stretcher, said retractable strap assemblies each comprising a spool container, an axle extending through said spool container, a spool rotatably mounted in said axle within said spool container, a strap wound about said spool, said strap having a distal end with a catch secured to said distal end of said strap, ratchet means for selectively precluding a rotation of said spool, and spring means for biasing said spool to rotate in a first direction;

a plurality of buckles secured to said stretcher, each of said buckles being operable to releasably capture said catch so as to secure said strap across said stretcher;

wherein said spool container includes an aperture extending therethrough, said aperture being shaped so as to define a flange, and further wherein said ratchet means comprises a ratchet secured to said spool, a release lever pivotally mounted to said spool container and extending from within said spool container through said aperture, a pawl pivotally mounted to said Spool container and coupled to said release lever, and a spring coupled to said pawl for biasing said pawl against said ratchet such that said spool can rotate in said first direction only, wherein said release lever is movable within said aperture and engagable to said flange so as to retain said pawl in a spaced relationship relative to said ratchet to permit rotation of said spool in said first direction and a second direction;

wherein said spring means comprises a spring retainer fixedly secured to said spool, a spiral spring positioned within said spring retainer, said spring being coupled to both said spring retainer and said axle for causing said spool to rotate in said first direction;

and at least one cable having a first end secured to said release lever for selectively, remotely disengaging said pawl from said ratchet, said cable having a second end coupled to said buckle for selectively, remotely actuating said buckle to release said catch.

2. The retractable strap apparatus as recited in claim 1, and further comprising a pulley rotatably mounted to said stretcher, and a handle coupled to said pulley for selectively rotating said pulley, wherein said cable is secured to said pulley such that a rotation of said pulley effects a disengaging of said pawl from said ratchet and an actuating of said buckle to release said catch.

3. The retractable strap apparatus as recited in claim 2, and further comprising an alarm means coupled to at least one of said retractable strap assemblies for creating a noise, said alarm means comprising a beeper mounted to said spool container, a battery, and a sensor movably mounted to said spool container, said sensor being operable to effect electrical communication between said battery and said beeper when said strap is substantially wound around said spool.

\* \* \* \* \*